(12) United States Patent
Mori et al.

(10) Patent No.: US 6,642,395 B1
(45) Date of Patent: Nov. 4, 2003

(54) ACETALSULFONATE DERIVATIVE, PROCESS FOR PRODUCING THE SAME, AND PROCESS FOR PRODUCING STYRENE OXIDE DERIVATIVE

(75) Inventors: Hiroyuki Mori, Yokohama (JP); Hikari Morita, Otake (JP); Yoshimasa Kobayashi, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 10/130,284

(22) PCT Filed: Nov. 28, 2000

(86) PCT No.: PCT/JP00/08374

§ 371 (c)(1), (2), (4) Date: May 29, 2002

(87) PCT Pub. No.: WO01/40168

PCT Pub. Date: Jun. 7, 2001

(30) Foreign Application Priority Data

Nov. 29, 1999 (JP) .............................. 11-338047
Nov. 29, 1999 (JP) .............................. 11-338048

(51) Int. Cl.$^7$ .................... C07C 309/00; C07D 407/00; C07D 303/00
(52) U.S. Cl. .......................... 549/414; 549/513; 558/44
(58) Field of Search ........................... 558/44; 549/513, 549/414

(56) References Cited

U.S. PATENT DOCUMENTS 4,391,826 A 7/1983 Mills et al. ................. 514/620

OTHER PUBLICATIONS

Tomoya Kitazume et al.: "The synthesis of optically active building blocks carrying a monofluoromethyl group" J. Flourine Chem., vol. 35, No. 3, pp. 477–488, 1987.
Masayuki Kameyama et al.: "Asymmetric radical reaction in the coordination sphere. 2. Asymmetric addition of alkane– and arenesulfonyl chlorides to olefins catalyzed by a ruthenium (II)–phosphine complex with chiral ligands" J. Org. Chem., vol. 52, No. 15, pp. 3312–3316, 1987.
Yutaka Nakamura et al.: "SmI2–mediated reductive enolization of alpha–hetero–substituted ketones and enantioselective protonation", Tetrahedron Lett., vol. 38, No. 15, pp. 2709–2712, 1994.
Yutaka Nakamura et al.: "Enantioselective protonation of samarium enolates derived from alpha–heterosubstituted ketones and lactone by SmI2–mediated reduction" Tetrahedron, vol. 55, No. 15, pates 4595–4620, 1999.
David Y. Curtin et al.: "Conversion of meso–hydrobenzoin with arylsulfonyl chlorides and base to trans–stilbene oxide and to 1,1–diphenyl–2–(p–toluenesulfonyl–oxy)ethylene", J. Org. Chem., vol. 21, pp. 1260–1263, May 21, 1956.
Ernest L. Eliel et al.: "A synthesis of optically active styrene oxide and other epoxides", J. Org. Chem., vol. 21, pp. 596–597, 1956.
Tsuneo Imamoto et al.: "An efficient synthesis of alpha–iodo derivatives of sulfones, sulfoximines, and phosphine oxides" Synthesis, pp. 983–985, 1985.
Jerome A. Berson et al.: "Asymmetric induction studies with optically active biphenyls. V. on the unreliability of absolute configurational assignments based on hydride reductions of phenylglyoxylates", J. Am. Chem., Soc., vol. 81, pp. 6456–6458, 1959.
Hartmuth C. Kolb et al.: "A simplified procedure for the sterospecific transformation of 1,2–diols into epoxides", Tetrahedron, vol. 48, No. 48, pp. 10515–10530, 1992.

*Primary Examiner*—Alan L. Rotman
*Assistant Examiner*—Raymond Covington
(74) *Attorney, Agent, or Firm*—Oblon, Spivak, McClelland, Maier & Neustadt, P.C.

(57) ABSTRACT

There are provided an acetalsulfonate derivative useful as an intermediate for medicines and agricultural chemicals, a process for industrially producing the derivative, and a process for industrially producing a styrene oxide derivative from the acetalsulfonate derivative or from a mandelic acid derivative.

A process for producing an acetalsulfonate derivative which comprises a first step of esterifying a mandelic acid derivative to form a mandelic ester derivative, a second step of protecting the mandelic ester derivative by an acetal to form an acetal derivative, a third step of reducing the acetal derivative to form an ethanediol derivative and a fourth step of reacting the ethanediol derivative with a sulfonyl chloride derivative. A process for producing a styrene oxide derivative which comprises a deprotecting step of deacetalizing the acetalsulfonate derivative and a step of epoxidizing the sulfonate derivative obtained in the deprotecting step with the aid of a base catalyst.

10 Claims, No Drawings

ACETALSULFONATE DERIVATIVE, PROCESS FOR PRODUCING THE SAME, AND PROCESS FOR PRODUCING STYRENE OXIDE DERIVATIVE

TECHNICAL FIELD

This invention relates to an acetalsulfonate derivative, a process for producing the same, and a process for producing a styrene oxide derivative using an acetalsulfonate derivative or a mandelic acid derivative as a starting material.

The starting materials, intermediates and final products of this invention can also be optically active substances. The compounds obtained according to this invention are useful as raw materials for medicines, agricultural chemicals, and the like and further, can give, in good yield, styrene oxide derivatives and ethanolamine derivatives which are useful as raw materials for medicines, agricultural chemicals, and the like.

The acetalsulfonate derivative of this invention can be easily converted into the corresponding styrene oxide derivative by epoxidation. The styrene oxide derivative thus obtained can be converted into corresponding ethanolamine derivatives by a reaction with various amines.

BACKGROUND ART

With regard to a process for producing an acetalsulfonate derivative, there can be considered, for example, a process which comprises converting an ethanediol derivative into a sulfonate derivative, followed by protection with an acetal. This process, however, has a problem in that it has a poor selectivity in converting an ethanediol derivative into a sulfonate derivative and hence an intended product cannot be isolated in high yield (J. Org. Chem., 21, 1260 (1956))

As to a process for producing a styrene oxide derivative, there is well known a process which comprises epoxidizing a 2-hydroxy-2-phenylethyl sulfonate derivative or a 2-hydroxy-2-phenylethyl halide derivative by use of a base (J. Org. Chem. 21,597 (1956)).

However, the 2-hydroxy-2-phenylethyl sulfonate derivative or the 2-hydroxy-2-phenylethyl halide derivative which are the materials used in the above-mentioned process are difficult to obtain in high purity. Accordingly, the epoxidation reaction has previously been conducted by using, as such, the above-mentioned derivatives mingled with their positional isomers, i.e., a 2-hydroxy-1-phenylethyl sulfonate derivative or 2-hydroxy-1-phenylethyl halide derivative, and a disulfonate derivative or dihalide derivative (Synthesis, 1985,983) (U.S. Pat. No. 4391826). In this process, when disulfoante derivative or dihalide derivative is mingled into the starting material, it is apt to cause difficulty in purification of the product, resulting in lowering of the yield. Still, when a position isomer is mingled, though the process has no problem in producing a racemic substance, it is apt to cause lowering of optical purity in case an optically active substance is produced.

Although an acetalsulfonate derivative and styrene oxide derivative are useful as an intermediate for medicines and agricultural chemicals, previous processes for producing them have problems as described above. Accordingly, a development of an industrial process for producing the derivatives has been eagerly awaited which is highly safe, simple and economical and gives good yield.

DISCLOSURE OF THE INVENTION

The present inventors have made extensive studies to achieve the above-mentioned object. As the result, the inventors have found that an acetalsulfonate derivative can be produced in high purity and high yield by using an inexpensive mandelic acid derivative as a starting material and that a styrene oxide derivative can be produced in high purity and high yield by using an acetalsulfonate derivative or a mandelic acid derivative as a starting material. This invention has been attained on the basis of the above finding.

Thus, the first aspect of this invention relates to an acetalsulfonate derivative which is represented by the following formula (1)

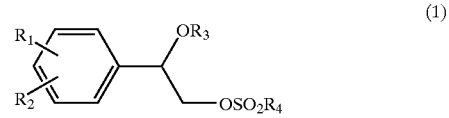

(1)

wherein $R_1$ and $R_2$ can be same as or different from each other and each denote a hydrogen atom, halogen atom, hydroxyl group, a straight or branched chain alkyl group having 1–4 carbon atoms optionally substituted with a halogen, a straight or branched chain alkoxy group having 1–4 carbon atoms optionally substituted with a halogen, amino group optionally substituted, nitro group or trifluoromethyl group, or $R_1$ and $R_2$ together denote a lower alkylenedioxy group; $R_3$ denotes 3,4,5,6-tetrahydro-2H-pyran-2-yl group or 1-methoxy-1-methylethyl group, and $R_4$ denotes a straight or branched chain alkyl group having 1–4 carbon atoms or a phenyl group optionally substituted.

The second aspect of this invention relates to a process for producing an acetalsulfonate derivative represented by the above formula (1) which comprises:

(a) a first step of esterifying a mandelic acid derivative represented by the following formula (2)

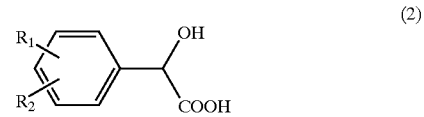

(2)

wherein $R_1$ and $R_2$ are the same as defined above, (b) a second step of protecting by an acetal a mandelic ester derivative represented by the following formula (3) obtained in the first step,

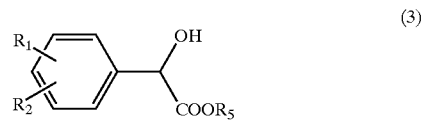

(3)

wherein $R_1$ and $R_2$ are the same as defined above and $R_5$ denotes a straight or branched chain alkyl group having 1–4 carbon atoms, (c) a third step of reducing an acetal derivative represented by the following formula (4) obtained in the second step,

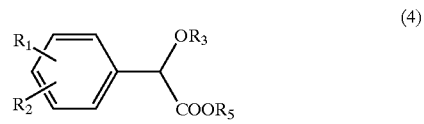

(4)

wherein $R_1$, $R_2$, $R_3$ and $R_5$ are the same as defined above, and (d) a fourth step of reacting with a sulfonyl chloride derivative an ethanediol derivative represented by the following formula (5) obtained in the third step,

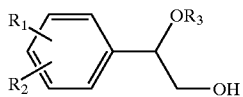
(5)

wherein $R_1$, $R_2$ and $R_3$ are the same as defined above.

The third aspect of this invention relates to a process for producing a styrene oxide derivative represented by the following formula (6)

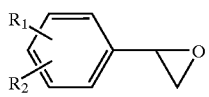
(6)

wherein $R_1$ and $R_2$ are the same as defined above, which comprises:

(e) a deprotecting step of deprotecting the acetalsulfonate derivative represented by the following formula (1)

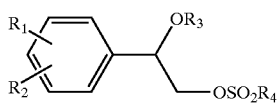
(1)

wherein $R_1$, $R_2$, $R_3$ and $R_4$ are the same as defined above, and (f) an epoxidizing step of epoxidizing a sulfoante derivative represented by the following formula (7) obtained in the above-mentioned deprotecting step, with the aid of a base catalyst,

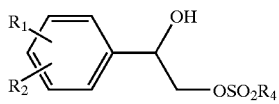
(7)

wherein $R_1$, $R_2$ and R4 are the same as defined above.

The fourth aspect of this invention relates to a process for producing the styrene oxide derivative represented by the above-mentioned formula (6) from a mandelic acid derivative through serial processes, said styrene oxide derivative being represented by the following formula (6),

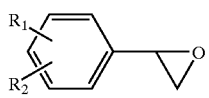
(6)

wherein $R_1$ and $R_2$ are the same as defined above, which comprises:

(a) a first step of esterifying a mandelic acid derivative represented by the following formula (2)

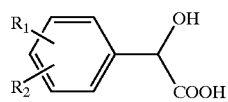
(2)

wherein $R_1$ and $R_2$ are the same as defined above, (b) a second step of protecting by an acetal a mandelic ester derivative represented by the following formula (3) obtained in the above-mentioned first step

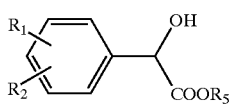
(3)

wherein $R_1$ $R_2$ and $R_5$ are the same as defined above, c) a third step of reducing an acetal derivative represented by the following formula (4) obtained in the above-mentioned second step

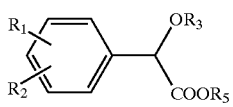
(4)

wherein $R_1$, $R_2$, $R_3$ and $R_5$ are the same as defined above, (d) a fourth step of reacting with a sulfonyl chloride derivative an ethanediol derivative represented by the following formula (5) obtained in the above-mentioned third step

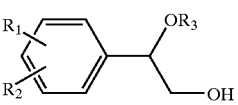
(5)

wherein $R_1$, $R_2$ and $R_3$ are the same as defined above, (e) a deprotecting step of deprotecting an acetalsulfonate derivative represented by the following formula (1) obtained in the above-mentioned fourth step

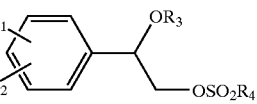
(1)

wherein $R_1$, $R_2$, $R_3$ and $R_4$ are the same as defined above, and (f) an epoxidizing step of epoxidizing a sulfonate derivative represented by the following formula (7) obtained in the above-mentioned deprotecting step, with the aid of a base catalyst

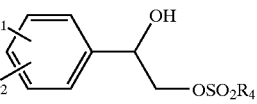
(7)

wherein $R_1$, $R_2$ and $R_4$ are the same as defined above,

Some embodiments of this invention are described further in detail below.

The acetalsulfonate derivative of this invention is represented by the above-mentioned formula (1), wherein $R_1$ and $R_2$ can be same as or different from each other and each denote a hydrogen atom, halogen atom, hydroxyl group, a straight or branched chain alkyl group having 1–4 carbon atoms optionally substituted with a halogen, a straight or branched chain alkoxy groups having 1–4 carbon atoms optionally substituted with a halogen, amino group optionally substituted, nitro group or trifluoromethyl group, or $R_1$ and $R_2$ together denote a lower alkylenedioxy group.

The straight or branched chain alkyl group having 1–4 carbon atoms optionally substituted with a halogen can be, for example, methyl group, ethyl group, n-propyl group, isopropyl group, n-butyl group, isobutyl group, sec-butyl group, tert-butyl group, trifluoromethyl group. and trichloromethyl group. The straight or branched chain alkoxy group having 1–4 carbon atoms optionally substituted with a halogen can be, for example, methoxy group, ethoxy group, n-propoxy group, isopropoxy group, n-butoxy group, sec-butoxy group, tert-butoxy group and trifluoromethoxy group. The amino group optionally substituted can be, for example, amino group, methylamino group, dimethylamino group, methylethylaminno group, morpholino group, piperidino group, pyrrolyl group, imidazolyl group and triazolyl group. The halogen atom can be a fluorine, chlorine, bromine or iodine atom. The lower alkylenedioxy group formed conjointly by $R_1$ and $R_2$ together can be, for example, the methylenedioxy group and ethylenedioxy group.

In the above-mentioned formula (1), $R_3$ denotes 3,4,5,6-tetrahydro-2H-pyran-2-yl group or 1-methoxy-1-methylethyl group; $R_4$ denotes a straight or branched chain alkyl group having 1–4 carbon atoms or a phenyl group optionally substituted. The straight or branched chain alkyl group having 1–4 carbon atoms can be, for example, methyl group, and the phenyl group optionally substituted can be, for example, p-tolyl group.

Specific examples of the acetalsulfonate derivative of this invention include 2-phenyl-2-(3,4,5,6-tetrahydro-[2H]-pyran-2-yloxy)ethyl methanesulfonate, 2-(2-chlorophenyl)-2-(1-methoxy-1-methylethyloxy)ethyl methanesulfonate, 2-(3-chlorophenyl)-2-(3,4,5,6-tetrahydro-[2H]-pyran-2-yloxy)ethyl methanesulfonate, 2-(4-chlorophenyl)-2-(3,4,5,6-tetrahydro-[2H]-pyran-2-yloxy)ethyl methanesulfonate, 2-(2-methylphenyl)-2-(1-methoxy-1-methylethyloxy)ethyl methanesulfonate, 2-(3-methylpheny)-2-(3,4,5,6-tetrahydro-[2H]-pyran-2-yloxy)ethyl methanesulfonate, 2-(4-methylphenyl)-2-(3,4,5,6-tetrahydro-[2H]-pyran-2-yloxy)ethyl methanesulfonate, 2-(2-hydroxyphenyl)-2-(1-methoxy-1-methylethyloxy)ethyl methanesulfonate, 2-(3-hydroxyphenyl)-2-(3,4,5,6-tetrahydro-[2H]-pyran-2-yloxy)ethyl methanesulfonate, 2-(4-hydroxyphenyl)-2-(3,4,5,6-tetrahydro-[2H]-pyran-2-yloxy)ethyl methanesulfonate, 2-(2-methoxyphenyl)-2-(3,4,5,6-tetrahydro-[2H]-pyran-2-yloxy)ethyl methanesulfonate, 2-(3-methoxyphenyl)-2-(1-methoxy-1-methylethyloxy)ethyl methanesulfonate, 2-(4-methoxyphenyl)-2-(3,4,5,6-tetrahydro-[2H]-pyran-2-yloxy) ethyl methanesulfonate, 2-(2-trifluoromethylphenyl)-21-methoxy-1-methylethyloxy)ethyl methanesulfonate, 2-(3-trifluoromethylphenyl)-2-(3,4,5,6-tetrahydro-[2H]-pyran-2-yloxy)ethyl methanesulfonate, 2-(4-trifluoromethylphenyl)-2-(3,4,5,6-tetrahydro-[2H]-pyran-2-yloxy)ethyl methanesulfonate, 2-(2-aminophenyl)-2-(3,4,5,6-tetrahydro-[2H]-pyran-2-yloxy)ethyl methanesulfonate, 2-(3-aminophenyl)-2-(3,4,5,6-tetrahydro-[2H]-pyran-2-yloxy)ethyl methanesulfonate, 2-(4-aminophenyl)-2-(1-methoxy-1-methylethyloxy)ethyl methanesulfonate, 2-(2-nitrophenyl)-2-(3,4,5,6-tetrahydro-[2H]-pyran-2-yloxy) ethyl methanesulfonate, 2-(3-nitrophenyl)-2-(3,4,5,6-tetrahydro-[2H]-pyran-2-yloxy)ethyl methanesulfonate, 2-(4-nitrophenyl)-2-(3,4,5,6-tetrahydro-[2H]-pyran-2-yloxy)ethyl methanesulfonate, 2-(2,4-dichlorophenyl)-2-(3,4,5,6-tetrahydro-[2H]-pyran-2-yloxy)ethyl methanesulfonate, 2-(2,4-difluorophenyl)-2-(3,4,5,6-tetrahydro-[2H]-pyran-2-yloxy)ethyl methanesulfonate, 2-(3,4-methylenedioxyphenyl)-2-(3,4,5,6-tetrahydro-[2H]-pyran-2-yloxy)ethyl methanesulfonate, 2-phenyl-2-(1-methoxy-1-methylethyloxy)ethyl p-toluenesulfonate, 2-(2-chlorophenyl)-2-(3,4,5,6-tetrahydro-[2H]-pyran-2-yloxy)ethyl p-toluenesulfonate, 2-(3-chlorophenyl)-2-(3,4,5,6-tetrahydro-[2H]-pyran-2-yloxy)ethyl p-toluenesulfonate, 2-(4-chlorophenyl)-2-(1-methoxy-1-methylethyloxy)ethyl p-toluenesulfonate, 2-(2-methylphenyl)-2-(3,4,5,6-tetrahydro-[2H]-pyran-2-yloxy)ethyl p-toluenesulfonate, 2-(3-methylphenyl)-2-(3,4,5,6-tetrahydro-[2H]-pyran-2-yloxy)ethyl p-toluenesulfonate, 2-(4-methylphenyl)-2-(3,4,5,6-tetrahydro-[2H]-pyran-2-yloxy)ethyl p-toluenesulfonate, 2-(2-hydroxyphenyl)-2-(1-methoxy-1-methylethyloxy)ethyl p-toluenesulfonate, 2-(3-hydroxyphenyl)-2-(3,4,5,6-tetrahydro-[2H]-pyran-2-yloxy)ethyl p-toluenesulfonate, 2-(4-hydroxyphenyl)-2-(3,4,5,6-tetrahydro-[2H]-pyran-2-yloxy)ethyl p-toluenesulfonate, 2-(2-methoxyphenyl)-2-(3,4,5,6-tetrahydro-[2H]-pyran-2-yloxy)ethyl p-toluenesulfonate, 2-(3-methoxyphenyl)-2-(1-methoxy-1-methylethyloxy)ethyl p-toluenesulfonate, 2-(4-methoxyphenyl)-2-(3,4,5,6-tetrahydro-[2H]-pyran-2-yloxy)ethyl p-toluenesulfonate, 2-(2-trifluoromethylphenyl)-2-(3,4,5,6-tetrahydro-[2H]-pyran-2-yloxy)ethyl p-toluenesulfonate, 2-(3-trifluoromethylphenyl)-2-(1-methoxy-1-methylethyloxy)ethyl p-toluenesulfonate, 2-(4-trifluoromethylphenyl)-2-(3,4,5,6-tetrahydro-[2H]-pyran-2-yloxy)ethyl p-toluenesulfonate, 2-(2-aminophenyl)-2-(3,4,5,6-tetrahydro-[2H]-pyran-2-yloxy)ethyl p-toluenesulfonate, 2-(3-aminophenyl)-2-(1-methoxy-1-methylethyloxy)ethyl p-toluenesulfonate, 2-(4-aminophenyl)-2-(3,4,5,6-tetrahydro-[2H]-pyran-2-yloxy)ethyl p-toluene sulfonate, 2-(2-nitrophenyl)-2-(3,4,5,6-tetrahydro-[2H]-pyran-2-yloxy)ethyl p-toluenesulfonate, 2-(3-nitrophenyl)-2-(3,4,5,6-tetrahydro-[2H]-pyran-2-yloxy)ethyl p-toluenesulfonate, 2-(4-nitrophenyl)-2-(3,4,5,6-tetrahydro-[2H]-pyran-2-yloxy)ethyl p-toluenesulfonate, 2-(2,4-dichlorophenyl)-2-(3,4,5,6-tetrahydro-[2H]-pyran-2-yloxy)ethyl p-toluenesulfonate, 2-(2,4-difluorophenyl)-2-(3,4,5,6-tetrahydro-[2H]-pyran-2-yloxy)ethyl p-toluenesulfonate, and 2-(3,4-methylenediloxyphenyl)-2-(3,4,5,6-tetrahydro-[2H]-pyran-2-yloxy)ethyl p-toluenesulfonate. The above-mentioned acetalsulfonate derivatives can also be respectively optically active substances.

The mandelic acid derivative used as a raw material in this invention is represented by the above-mentioned formula (2), wherein $R_1$ and $R_2$ are the same as defined in the above formula (1).

Specific examples of the mandelic acid derivative defined as described above include mandelic acid, 2-chloromandelic acid, 3-chloromandelic acid, 4-chloromandelic acid, 2-methylmandelic acid, 3-methylmandelic acid, 4-methylmandelic acid, 2-hydroxymandelic acid, 3-hydroxymandelic acid, 4-hydroxymandelic acid, 2-methoxymandelic acid, 3-methoxymandelic acid,: 4-methoxymandelic acid, 2-trifluoromethylmandelic acid, 3-trifluoromethylmandelic acid, 4-trifluoromethylmandelic acid, 2-aminomandelic acid, 3-aminomandelic acid, 4-aminomandelic acid, 2-nitromandelic acid, 3-nitromandelic acid, 4-nitromandelic acid, 2,4-dichloromandelic acid, 2,4-difluoromandelic acid, and 3,4- methylenedioxymandelic acid. The above-mentioned mandelic acid derivatives can also be respectively optically active substances.

The mandelic acid derivative defined as described above can be easily converted, in the first step, into a corresponding mandelic ester derivative represented by the formula (3) by esterification. For example, it can be easily prepared in the presence of an acid catalyst in an alcohol, such as methanol, ethanol, propanol, isopropanol, n-butanol, isobutanol, sec-butanol and tert-butanol. In the mandelic ester derivative represented by the formula (3) obtained in the first step, $R_5$ is, for example, methyl, ethyl, n-propyl, isopropyl, n-butyl, isobutyl, sec-butyl or tert-butyl group.

In the esterification of the first step reaction, the alcohol can be used in excess to use it also as a solvent, but organic solvents other than alcohols can also be used. Examples of the organic solvent include aromatic hydrocarbons such as toluene and xylene, halogenated hydrocarbons such as methylene chloride and chloroform, ethers such as diethyl ether, diisopropyl ether, tetrahydrofuran, 1,4-dioxane and tert-butyl methyl ether, ester type solvents such as ethyl acetate and methyl acetate, and nitrile type solvents such as acetonitrile. These organic solvents can be used each alone or as a mixture thereof.

The acid catalyst which can be used in the first step can be, for example, sulfuric acid, hydrochloric acid, nitric acid, phosphoric acid, p-toluenesulfonic acid and methanesulfonic acid.

The reaction temperature of the first step can be in the range of: 0–100° C., preferably 20° C.–80° C. The reaction period of time, which can vary according to the acid used and the reaction temperature, can be usually not more than 12 hours, preferably in the range of 0.5–6 hours.

The mandelic ester derivative of the formula (3) obtained in the first step can be easily converted, in the second step, into a corresponding acetal derivative represented by the formula (4), for example, by reacting it with an acetalizing agent under acidic conditions by use of an acid catalyst. In the formula (4), $R_3$ and $R_5$ have the same meaning as described above.

The acetalizing agent which can be used in the second step can be, for example, 1-methoxy-1-methylethyl or 3,4-dihydro-2H-pyran.

The acid catalyst which can be used in the second step can be, for example, acetic acid, trifluoroacetic acid, p-toluenesulfonic acid and methanesulfonic acid.

The reaction solvent which can be used in the second step can be organic solvents inert to the reaction used each alone or as a mixture thereof, for example, aromatic hydrocarbons such as toluene and xylene, halogenated hydrocarbons such as methylene chloride and chloroform, ethers such as diethyl ether, diisopropyl ether, tetrahydrofuran, 1,4-dioxane and t-butyl methyl ether, ester type solvents such as ethyl acetate and methyl acetate, and nitrile type solvents such as acetonitrile.

The reaction temperature of the second step can be in the range of 0–100° C., preferably 10–40° C. The reaction period of time, which can vary according to the acid used and the reaction temperature, can be usually not more than 12 hours, preferably in the range of 0.5–6 hours.

The acetal derivative of the formula (4) obtained in the second step can be easily converted, in the third step, into the corresponding ethanediol derivative represented by the formula (5) by a reduction thereof.

A reducing agent which can be used in the third step can be, for example, sodium borohydride, lithium aluminum hydride and sodium dihydrobis(2-methoxyethoxy) aluminate, preferably sodium dihydrobis(2-methoxyethoxy) aluminate.

A reaction solvent which can be used in the third step can be organic solvents inert to the reaction, used each alone or as a mixture thereof, for example, aromatic hydrocarbons such as toluene and xylene, halogenated hydrocarbons such as methylene chloride and chloroform, ethers such as diethyl ether, diisopropyl ether, tetrahydrofuran, 1,4-dioxane and t-butyl methyl ether, ester type solvents such as ethyl acetate and methyl acetate, and nitrile type solvents such as acetonitrile.

A reaction temperature of the third step can be in the range of −20 to 100° C., preferably 0–40° C. A reaction period of time can be usually not more than 12 hours, preferably in the range of 0.5–6 hours.

The ethanediol derivative of the formula (5) obtained in the third step can be easily converted, in the fourth step, into a corresponding acetalsulfonate derivative represented by the formula (1) by reacting it with a sulfonyl chloride derivative.

The sulfonyl chloride derivative used in the fourth step can be, for example, p-toluenesulfonyl chloride and methanesulfonyl chloride.

A base can be used in the fourth step. The base can be, for example, trialkylamines such as trimethylamine and triethylamine, cyclic tertiary amides such as N-methylmorpholine and N-methylpiperidine, N,N-dimethylaniline, pyridine, sodium hydroxide and potassium hydroxide.

A reaction solvent which can be used in the fourth step can be organic solvents inert to the reaction, used each alone or as a mixture thereof, for example, aromatic hydrocarbons such as toluene and xylene, halogenated hydrocarbons such as methylene chloride and chloroform, ethers such as diethyl ether, diisopropyl ether, tetrahydrofuran, 1,4-dioxane and t-butyl methyl ether, ester type solvents such as ethyl acetate and methyl acetate, nitrile type solvents such as acetonitrile, and water.

A reaction temperature of the fourth step can be in the range of −20 to 100° C., preferably 0–40° C. A reaction period of time can be usually not more than 12 hours, preferably in the range of 0.5–6 hours.

The intended acetalsulfonate can be easily purified after a completion of the reaction, according to necessity, for example by using a column.

When optically active mandelic acid derivatives are used as the starting compounds and subjected to reaction by the above-mentioned method, it has been found that the acetalsulfonate derivatives obtained have respective corresponding configurations and thus the configurations have been retained. Thus, it has become possible to provide from an optically active mandelic acid derivative a corresponding optically active acetalsulfonate derivative while retaining the configuration. The optical purity of the optically active acetalsulfonate derivative obtained was determined by high performance liquid chromatography using an optical resolution column.

In the process for producing a styrene oxide derivative of the third aspect of this invention, specific examples of the acetalsulfonate derivative used as the starting material can be the acetalsulfonate derivatives of the first aspect of this invention described above and the acetalsulfonate derivatives obtained by the method of the second aspect of this invention described above.

The protecting step of the step (e) in the third aspect of this invention is a step of deacetalizing the acetalsulfonate derivative represented by the formula (1) of the starting material to form a sulfonate derivative represented by the formula (7). In the step (e), the acetalsulfonate derivative can be easily deprotected, for example, by treating it with an acid.

The acid can be, for example, inorganic acids such as hydrochloric acid, sulfuric acid and phosphoric acid, and organic acids such as formic acid, acetic acid, methanesulfonic acid and p-toluenesulfonic acid.

A reaction solvent which can be used in the step (e) can be protic solvents, such as water, methanol, ethanol and isopropanol, used alone or as a mixture thereof with an aprotic solvent. The aprotic solvents used can be, for example, aromatic hydrocarbons such as toluene and xylene, aliphatic hydrocarbons such as hexane, heptane and cyclohexane, halogenated hydrocarbons such as methylene chloride and chloroform, esters such as methyl acetate and ethyl acetate, ethers such as dioxane, tetrahydrofuran, diisopropyl ether and t-butyl methyl ether, and acetonitrile.

A reaction temperature of the step (e) can be 0–100° C., preferably 20–80° C. A reaction period of time, which can vary according to the acid, solvent and reaction temperature used, can be usually not more than 12 hours, preferably 0.5–6 hours.

The epoxidizing step of the step (f) in the third aspect of this invention is a step of epoxidizing the sulfonate derivative represented by the formula (7) obtained in the step (e) in the presence of a base catalyst.

The base catalyst used can be, for example, alkali metal alcoholates such as sodium methoxide and sodium ethoxide, alkali metal salts such as sodium hydroxide and potassium hydroxide, and alkali carbonates such as sodium carbonate and potassium carbonate.

A reaction solvent which can be used in the step (f) can be protic solvents, such as water, methanol, ethanol and:isopropanol, used each alone or in combination or as a mixture thereof with an aprotic solvent. When an organic solvent immiscible with water is used as a mixture with water, the reaction can be conducted in a double-layer system. The organic solvent immisible with water can be aromatic hydrocarbons such as toluene and xylene, halogenated hydrocarbons such as methylene chloride and chloroform, ethers such as diisopropyl ether and t-butyl methyl ether, and esters such as ethyl acetate and methyl acetate. Examples of organic solvent miscible with water include alcohols such as methanol, ethanol and isopropanol, ethers such as dioxane, tetrahydrofuran and dimethoxyethane, amides such as N,N-dimethylformamide and N,N-dimethylacetamide, and acetonitrile.

A reaction temperature of the step (f) can be in the range of 0–100° C., preferably 10–40° C. A reaction period of time, which can vary according to the base and reaction temperature used, can be usually not more than 12 hours, preferably 0.5–6 hours.

Specific examples of the styrene oxide derivative represented by the formula (6) obtained by the two steps of step (e) and step (f) from the acetalsulfonate derivative represented by the formula (1) include styrene oxide, 3-chlorostyrene oxide, 4-chlorostyrene oxide, 3,4-dichlorostyrene oxide, 4-methylstyrene oxide, 3,4-methylenedioxystyrene oxide, 4-trifluoromethylstyrene oxide and 2-chlorostyrene oxide. The styrene oxide derivatives mentioned above can also be respectively optically active substances.

It has been found that when optically active acetalsulfonate derivatives are used as the starting compounds and subjected to reaction by the above-mentioned method, the styrene oxide derivatives obtained have respective corresponding configurations and thus the configurations have been retained. Thus, it has become possible to provide from an optically active acetalsulfonate derivative a corresponding optically active styrene oxide derivative while retaining the configuration. The optical purity of the optically active styrene oxide derivative was determined by high performance liquid chromatography using an optical resolution column.

In the process for producing a styrene oxide derivative of the fourth aspect of this invention, wherein the styrene oxide derivative represented by the formula (6) is produced from the mandelic acid derivative represented by the formula (2) through serial processes, the mandelic acid derivative used is the same as that represented by the formula (2) in the second aspect of this invention, the first step of esterifying the mandelic acid derivative is the same as the first step in the second aspect of this invention, the mandelic acid derivative obtained in the first step is the same as that represented by the formula (3) in the second aspect of this invention, the second step of protecting the mandelic acid derivative by an acetal is the same as the second step in the second aspect of this invention, the acetal derivative obtained in the second step is the same as that represented by the formula (4) in the second aspect of this invention, the third step of reducing the acetal derivative is the same as the third step in the second aspect of this invention, the ethanediol derivative obtained in the third step is the same as that represented by the formula (5) in the second aspect of this invention, the fourth step of reacting the ethanediol derivative with a sulfonyl chloride derivative is the same as the fourth step in the second aspect of this invention, the acetalsulfonate derivative obtained in the fourth step is the same as the acetalsulfonate derivative represented by the formula (1) of the first aspect of this invention and the same as the acetalsulfonate derivative obtained by the process of the second aspect of this invention, the: deprotecting step (step (e)) of deprotecting the acetalsulfonate derivative is the same as the step (e) in the third aspect of this invention, the sulfonate derivative obtained in the step (e) is the same as that represented by the formula (7) in the third aspect of this invention, and the epoxidizing step (step (f)) of epoxidizing the sulfonate derivative with the aid of a base catalyst is the same as the step (f) in the third aspect of this invention.

BEST MODE FOR CARRYING OUT THE INVENTION

This invention is described further in detail below with reference to Examples and Comparative Examples, but the invention is in no way limited to the Examples.

EXAMPLE 1

Preparation of (R)-2-phenyl-2-(3,4,5,6-tetrahydro-[2H]-pyran-2-yloxy)ethyl Methanesulfonate 1) Preparation of (R)-mandelic Acid Methyl Ester Into methanol (20 ml) were added (R)-mandelic acid (5.0 g) and p-toluenesulfonic acid (0.1 g), and the resulting mixture was heated under reflux for 2 hours. The reaction mixture was cooled, then neutralized, and concentrated. Ethyl acetate and water were added to the resulting residue, and the organic layer was collected by layer separation. The organic layer was washed with a saturated aqueous sodium chloride solution and dried with anhydrous magnesium sulfate. The desiccant was removed by filtration, and the solvent was distilled off from the filtrate to obtain a colorless oily compound mentioned above (5.35 g, 97.9%).

2) Preparation of (R)-2-Phenyl-2-(3,4,5,6-tetrahydro-[2H]-pyran-2-yloxy)mandelic Acid Methyl Ester Into toluene (20 ml) were added (R)-mandelic acid methyl ester (5.0 g) obtained in 1) above and p-toluenesulfonic acid (0.1 g), and thereto was dropwise added 3,4-dihydro-2H- pyran (2.55 g) with ice cooling. The resulting mixture was stirred at the same temperature for 1 hour, the reaction mixture was washed with a saturated aqueous sodium hydrogen carbonate solution, then the organic layer was washed with a saturated aqueous sodium chloride solution and dried with anhydrous magnesium sulfate. The desiccant was removed by filtration and the solvent was distilled off to obtain a colorless compound mentioned above (7.35 g, 97.5%).

3) Preparation of (R)-2-Phenyl-2-(3,4,5,6-tetrahydro-[2H]-pyran-2-yloxy)ethanol

Into toluene (15 ml) was added (R)-2-phenyl-2-(3,4,5,6-tetrahydro-[2H]-pyran-2-yloxy)mandelic acid methyl ester (7.0 g) obtained in 2) above, and thereto was dropwise added a 70% sodium dihydrobis(2-methoxyethoxy)aluminate toluene solution (8.73 g) with ice cooling. The resulting mixture was stirred at the same temperature for 1 hour, the reaction mixture was added into a 30% aqueous (+)-potassium sodium tartrate solution (31.3 g), then stirred for 1 hour, and the organic layer was separated. The organic layer obtained was washed with water and further with a saturated aqueous sodium chloride solution and then dried with anhydrous magnesium sulfate. The desiccant was removed by filtration and the solvent was distilled off to obtain a colorless oily compound mentioned above (6.10 g, 97.9%).

4) Preparation of (R)-2-phenyl-2-(3,4,5,6-tetrahydro-[2H]-pyran-2-yloxy)ethyl Methanesulfonate Into toluene (20 ml) were added (R)-2-phenyl-2-(3,4,5,6-tetrahydro-[2H]-pyran-2-yloxy)ethanol (6.0 g) and triethylamine (5.4 g), then thereto was dropwise added methanesulfonyl,;chloride (3.1 g) with ice cooling. The resulting mixture was stirred at the same temperature for 1 hour, the reaction mixture was washed with water, then the organic layer was washed with a saturated aqueous sodium chloride solution and dried with anhydrous magnesium sulfate. The desciccant was filtered off and then the solvent was distilled off to obtain a colorless oily compound mentioned above (7.8 g, 96.2%). The optical purity of the product obtained was 99.9% e.e.

The overall yield from 1) to 4) was 89.9%. $^1$H-NMR (CDCl$_3$)δ: 1.48–11.77 (6H, m), 2.97 and 3.01 (3H, s), 3.31–3.53 and 3.92–3.97 (2H, m), 4.25–4.41 (2H, m), 4.49–4.96 (1H, m), 4.90–5.04 (1H, m), 7.14–7.43 (5H, m)

EXAMPLE 2

Preparation of (R)-2-(3-Chlorophenyl)-2-(3,4,5,6-tetrahydro-[2H]-pyran-2-yloxy)ethyl Methanesulfonate 1) Preparation of (R)-3-chloromandelic Acid Methyl Ester Into methanol (20 ml) were added (R)-3-chloromandelic acid (5.0 g) and p-toluenesulfonic acid (0.1 g), and the resulting mixture was heated under reflux for 2 hours. The reaction mixture was cooled, then neutralized and concentrated. Ethyl acetate and water were added to the resulting residue and the organic layer was collected by layer separation. The organic layer was washed with a saturated aqueous sodium chloride solution and then dried with anhydrous magnesium sulfate. The desiccant was filtered off and then the solvent was distilled off to obtain a colorless oily compound mentioned above (5.27 g, 98.3%).

2) Preparation of (R)-2-(3-Chlorophenyl)-2-(3,4,5,6-tetrahydro-[2H]-pyran-2-yloxy)mandelic Acid Methyl Ester Into toluene (20 ml) were added (R)-3-chloromandelic acid methyl ester (5.2 g) obtained in 1) above and p-toluenesulfonic acid (0.1 g), thereto was then dropwise added 3,4-dihydro-2H-pyran (2.19 g) with ice-cooling. The resulting mixture was stirred at the same temperature for 1 hour, the reaction mixture was washed with a saturated aqueous sodium hydrogen carbonate solution, then the organic layer was further washed with a saturated aqueous sodium chloride solution and dried with anhydrous magnesium sulfate. The desiccant was filtered off and then the solvent was distilled off to obtain a colorless oily compound mentioned above (7.20 g, 97.5%).

3) Preparation of (R)-2-(3-Chlorophenyl)-2-(3,4,5,6-tetrahydro-[2H]-pyran-2-yloxy)ethanol Into toluene (15 ml) were added (R)-2-(3-chlorophenyl)-2-(3,4,5,6-tetrahydro-[2H]-pyran-2-yloxy)-mandelic acid methyl ester (7.0 g) obtained in 2) above and then, under ice cooling and dropwise, a 70% sodium dihydrobis(2-methoxyethoxy)aluminate toluene solution (7.67 g). The resulting mixture was stirred at the same temperature for 1 hour. Then the reaction mixture was added into a 30% aqueous (+)-potassium sodium tartrate solution (27.6 g), the resulting mixture was stirred for 1 hour and then the organic layer was separated. The organic layer obtained was washed with water and further with a saturated aqueous sodium chloride solution and then dried with anhydrous magnesium sulfate. The desciccant was filtered off and then the solvent was distilled off to obtain a colorless oily compound mentioned above (6.2 g, 98.1%).

4) Preparation of (R);-2-(3-Chlorophenyl)-2-(3,4,5,6-tetrahydro-[2H]-pyran-2-yloxy)ethyl Methanesulfonate Into toluene (20 ml) were added (R)-2-(3-chlorophenyl)-2-(3,4,51,6-tetrahydro-[2H]-pyran-2-yloxy)ethanol obtained in 3) above (6.0 g) and triethylamine (4.7 g) and further, under ice-cooling and dropwise, methanesulfonyl chloride (2.68 g). The resulting mixture was stirred at the same temperature for 1 hour. The reaction mixture was washed with water, then the organic layer was further washed with a saturated aqueous sodium chloride solution and dried with anhydrous magnesium sulfate. The desiccant was filtered off and then the solvent was distilled off to obtain a colorless oily compound mentioned above (7.6 g, 97.1%). The optical purity of the product obtained was 99.9% e.e.

$^1$H-NMR (CDCl$_3$)δ: 1.48–1.77 (6H, m), 2.97 and 3.01 (3H, s), 3.31–3.53 and 3.92–3.97 (2H, m), 4.25–4.41 (2H, m), 4.49–4.96 (1H, m), 4.90–5.04 (1H, m), 7.23–7.42 (4H, m).

The overall yield from 1) to 4) was 91.3%.

EXAMPLE 3

Preparation of (R)-2-(4-chlorophenyl)-2-(1-methoxy-1-methylethyloxy)ethyl Metanesulfonate 1) Preparation of (R)-4-chloromandelic Acid Methyl Ester Into toluene (20 ml) were added methanol (3.0 g), (R)-4-chloromandelic acid (5.0 g) and p-toluenesulfonic acid (0.1 g), and the resulting mixture was heated under reflux for 2 hours. The reaction mixture was cooled, then washed with a saturated aqueous sodium hydrogen carbonate solution, and then the organic layer was washed with a saturated aqueous sodium chloride solution and dried with anhydrous magnesium sulfate. The desiccant was filtered off and the solvent was distilled off to obtain a colorless oily compound mentioned above (5.23 g, 97.5%).

2) Preparation of (R)-2-(4-Chlorophenyl)-2-(1-methoxy-1-methylethyloxy)mandelic Acid Methyl Ester Into methylene chloride (20 ml) were added (R)-4-chloromandelic acid methyl ester obtained in 1) above (5.0 g) and p-toluenesulfonic acid (0.1 g) and further, under ice-cooling and dropwise, 2-methoxypropene (1.89 g). The resulting mixture was stirred at the same temperature for 1 hour. The reaction mixture was washed with a saturated aqueous sodium hydrogen carbonate solution, then the organic layer was further washed with a saturated aqueous sodium chloride solution and dried with anhydrous magnesium sulfate. The desiccant was filtered off and then the solvent was distilled off to obtain a colorless oily compound mentioned above (6.59 g, 97.0%).

3) Preparation of (R)-2-(4-Chlorophenyl)-2-(1-methoxy-1-methylethyloxy)ethanol

Into methanol (20 ml) were added (R)-2-(4-chlorophenyl)-2-(1-methoxy-1-methylethyloxy)mandelic acid methyl ester obtained in 2) above (6.0 g) and further, under ice-cooling, sodium borohydride (4.35 g). The resulting mixture was stirred at the same temperature, neutralized and the reaction mixture was concentrated. Ethyl acetate and water were added to the resulting residue and the organic layer was collected by layer separation. The organic layer was washed with a saturated aqueous sodium chloride solution and dried with anhydrous magnesium sulfate. The desiccant was filtered off and then the solvent was distilled off to obtain a colorless oily compound mentioned above (5.2 g, 96.7%).

4) Preparation of (R)-2-(4-Chlorophenyl)-2-(1-methoxy-1-methylethyloxy)ethyl Methanesulfonate Into methylene chloride (20 ml) were added (R)-2-(3-chlorophenyl)-2-(1-methoxy-1-methylethyloxy)ethanol obtained in 3) above (5.0 g) and triethylamine (3.9 g) and further, under ice-cooling and dropwise, methanesulfonyl chloride (2.46 g), and the resulting mixture was stirred at the same temperature for 1 hour. The reaction mixture was washed with water, and the organic layer was washed with a saturated aqueous sodium chloride solution and dried with anhydrous magnesium sulfate. The desiccant was filtered off and the solvent was distilled off to obtain a colorless oily compound mentioned above (6.33 g, 96.0%). The optical purity of the product obtained was 99.9% e.e.

The overall yield of 1) to 4) was 87.8%.

$^1$H-NMR (CDCl$_3$)δ: 1.48–1.77 (6H, m), 2.97 and 3.01 (3H, s), 3.31–3.53 and 3.92–3.97 (2H, m), 4.25–4.41 (2H, m), 4.49–4.96 (1H, m), 4.90–5.04 (1H, m), 15 7.21–7.40 (4H, m)

EXAMPLE 4

Preparation of (S)-2-(3-Chlorophenyl)-2-(3,4,5,6-tetrahydro-[2H]-pyran-2-yloxy)ethyl Methanesulfonate An experiment was conducted according to the same method as in Example 1 except for using (S)-3-chloromandelic acid as a starting material, to obtain the title compound in overall yield of 91.0%. The optical purity of the product obtained was 99.9% e.e.

EXAMPLE 5

Preparation of (R,S)-2-(3-Chlorophenyl)-2-(3,4,5,6-tetrahydro-[2H]-pyran-2-yloxy)ethyl p-Toluene-Sulfonate 1) Preparation of (R,S)-3-chloromandelic Acid Methyl Ester An experiment was conducted according to the same method as in Example 1 except for using (R,S)-3-chloromandelic acid as a starting material to obtain the title compound in 97.5% yield.

2) Preparation of (R,S)-2-(3-chlorophenyl)-2-(3,4,5,6-tetrahydro-[2H]-pyran-2-yloxy)mandelic Acid Methyl Ester According to the same method as in Example 1 except for using (R,S)-3-chloromandelic acid methyl ester as a starting material, a colorless oily compound mentioned above was obtained in 97.5% yield.

3) Preparation of (R,S)-2-(3-Chlorophenyl)-2-(3,4,5,6-tetrahydro-[2H]-pyran-2-yloxy)ethanol According to the same method as in Example 1 except for using (R,S)-2-(3-chlorophenyl)-2-(3,4,5,6-tetrahydro-[2H]-pyran-2-yloxy)mandelic acid methyl ester as a starting material, a colorless oily compound mentioned above was obtained in 97.0% yield.

4) Preparation of (R,S)-2-(3-Chlorophenyl)-2-(3,4,5,6-tetrahydro-[2H]-pyran-2-yloxy)ethyl p-Toluenesulfonate Into toluene (20 ml) were added (R)-2-(3-chlorophenyl)-2-(3,4,5,6-tetrahydro-[2H]-pyran-2-yloxy)ethanol obtained in 3) above (6.0 g) and triethylamine (4.7 g) and further, under ice-cooling and dropwise, p-toluenesulfonyl chloride (4.9 g), and the resulting mixture was stirred at the same temperature for 1 hour. The reaction mixture was washed with water and the organic layer was further washed with a saturated aqueous sodium chloride solution and dried with anhydrous magnesium sulfate. The desiccant was filtered off and then the solvent was distilled off to obtain a colorless oily compound mentioned above (9.1 g, 94.8%).

The overall yield from 1) to 4) was 87.4%.

EXAMPLE 6

Preparation of (R)-styrene Oxide

1) Preparation of (R)-2-hydroxy-2-phenylethyl Methanesulfonate

Into methanol (10 ml) were added (R)-2-phenyl-2-(3,4,5,6-tetrahydro-[2H]-pyran-2-yloxy)ethyl methanesulfonate (2.0 g) and hydrochloric acid (0.07 g), and the resulting mixture was stirred at room temperature for 3 hours. The reaction mixture was neutralized, concentrated, and then ethyl acetate and water were added to the resulting residue. The organic layer was collected by layer separation, washed with a saturated aqueous sodium chloride solution and dried with anhydrous magnesium sulfate. The desiccant was filtered off and then the solvent was distilled off to obtain a colorless oily compound mentioned above (1.4 g, 97.2%).

2) Preparation of (R)-styrene oxide

Into methanol (10 ml) were added (R)-2-hydroxy-2-phenylethyl methanesulfonate obtained in 1) above (1.4 g) and 28% NaOMe (1.25 g), and the resulting mixture was stirred at room temperature for 1 hours. The reaction mixture was neutralized, concentrated, and then ethyl acetate and water were added to the resulting residue. The organic layer was collected by layer separation, washed with a saturated aqueous sodium chloride solution and then dried with anhydrous magnesium sulfate. The desiccant was filtered off, then the solvent was distilled off under reduced pressure, and the resulting oily substance was distilled under reduced pressure to obtain a colorless oily compound mentioned above (0.7 g, 90.0%). The optical purity of the product obtained was 99.9% e.e. as determined by HPLC.

EXAMPLE 7

Preparation of (R)-3-chlorostyrene Oxide

1) Preparation of (R)-2-(3-chlorophenyl)-2-hydroxyethyl Methanesulfonate

Into methanol (10 ml) were added (R)-2-(3-chlorophenyl)-2-(3,4,5,6-tetrahydro-[2H]-pyran-2-yloxy) ethyl methanesulfonate (3.0 g) and hydrochloric acid (0.11 g), and the resulting mixture was stirred at room temperature for 3 hours. The reaction mixture was neutralized, concentrated, and ethyl acetate and water were added to the resulting residue. The organic layer was collected by layer separation, washed with a saturated aqueous sodium chloride solution and dried with anhydrous magnesium sulfate.

The desiccant was filtered off, and the solvent was distilled off under reduced pressure to obtain a colorless oily compound mentioned above (2.1 g, 93.5%).

2) Preparation of (R)-3-chlorostyrene Oxide

Into metanol (10 ml) were added (R)-2-(3-chlorophenyl)-2-hydroxyethyl methanesulfonate obtained in 1) above (2.1 g) and 28% NaOMe (1.6 g), and the resulting mixture was stirred at room temperature for 1 hour. The reaction mixture was neutralized, concentrated, and then ethyl acetate and water were added to the resulting residue. The organic layer was collected by layer separation, washed with a saturated aqueous sodium chloride solution and dried with anhydrous magnesium sulfate. The desiccant was filtered off, then the solvent was distilled off under reduced pressure, and the resulting oily substance was distilled under reduced pressure to obtain a colorless oily compound mentioned above (1.15 g, 88.8%). The optical purity of the product obtained was 99.9% e.e. as determined by HPLC.

EXAMPLE 8

Preparation of (R)-4-chlorostyrene Oxide

1) Preparation of (R)-2-(4-chlorophenyl)-2-hydroxyethyl Methanesulfonate

Into toluene (10 ml) were added 2-(4-chlorophenyl)-2-(3,4,5,6-tetrahydro-[2H]-pyran-2-yloxy)ethyl methanesulfonate (3.0 g), p-toluenesulfonic acid monohydrate (1.7 g) and methanol (0.5 g), and the resulting mixture was stirred at 50° C. for 1 hour. The reaction mixture was washed with a saturated aqueous sodium hydrogen carbonate solution, then with a saturated aqueous sodium chloride solution, and dried with anhydrous magnesium sulfate. The desiccant was filtered off and then the solvent was distilled off under reduced pressure to obtain a colorless oily compound mentioned above (2.0 g, 89.0%).

2) Preparation of (R)-4-chlorostyrene Oxide

Into toluene (10 ml) were added (R)-2-(4-chlorophenyl)-2-hydroxyethyl methanesulfonate obtained in 1) above (2.0 g) and 20% NaOH (10 ml), and the resulting mixture was stirred vigorously at room temperature for 1 hour. The reaction mixture was subjected to layer separation, the organic layer was washed with water, then with a saturated aqueous sodium chloride solution, and dried with anhydrous magnesium sulfate. The desiccant was filtered off, then the solvent was distilled off under reduced pressure, and the resulting oily substance was distilled under reduced pressure to obtain a colorless oily compound mentioned above (1.1 g, 89.2%). The optical purity of the product obtained was 99.9% e.e. as determined by HPLC.

EXAMPLE 9

Preparation of (S)-styrene Oxide

1) Preparation of (S)-2-phenyl-2-hydroxyethyl p-Toluenesulfonate

Into toluene (10 ml) were added (S)-2-phenyl-2-(1-methoxy-1-methylethyloxy)ethyl p-toluenesulfonate (3.0 g), p-toluenesulfonic acid monohydrate (1.7 g) and methanol (0.5 g), and the resulting mixture was stirred at 50° C. for 1 hour. The reaction mixture was washed with a saturated aqueous sodium hydrogen carbonate solution, then with a saturated aqueous sodium chloride solution, and dried with anhydrous magnesium sulfate. The desiccant was filtered off and then the solvent was distilled off under reduced pressure to obtain a colorless oily compound mentioned above (2.1 g, 88.0%).

2) Preparation of (S)-styrene Oxide

Into toluene (10 ml) were added (S)-2-phenyl-2-hydroxyethyl p-toluenesulfonate obtained in 1) above (2.0 g) and 20% NaOH (10 ml), and the resulting mixture was stirred vigorously at room temperature for 1 hour. The reaction mixture was subjected to layer separation, the organic layer was washed with water, then with saturated aqueous sodium chloride solution, and dried with anhydrous magnesium sulfate. The desiccant was filtered off and then the solvent was distilled off under reduced pressure. The resulting oily substance was distilled under reduced pressure to obtain a colorless oily compound mentioned above (0.74 g, 90.0%). The optical purity of the product obtained was 99.9% e.e. as determined by HPLC.

EXAMPLE 10

Preparation of (S)-3-chlorostyrene Oxide

Into toluene (10 ml) were added (S)-2-(3-chlorophenyl)-2-(3,4,5,6-tetrahydro-[2H]-pyran-2-yloxy)ethyl methanesulfonate (3.0 g), p-toluenesulfonic acid monohydrate (1.7 g) and methanol (0.5 g), and the resulting mixture was:stirred at 50° C. for 1 hour. The reaction mixture was Washed with a saturated aqueous sodium hydrogen carbonate solution and then with a saturated aqueous sodium chloride solution. To the organic layer was added 20% NaOH (10 ml) and the resulting mixture was stirred vigorously at room temperature for 1 hour. The reaction mixture was subjected to layer separation, and the organic layer was washed with water, then with a saturated aqueous sodium chloride solution and dried with anhydrous magnesium sulfate. The desiccant was filtered off, then the solvent was distilled off, and the resulting oily substance was distilled under reduced pressure to obtain a colorless oily compound mentioned above (1.27 g, 91.7%). The optical purity of the product obtained was 99.9% e.e. as determined by HPLC.

EXAMPLE 11

Preparation of (S)-3-chlorostyrene Oxide

According to the same method as in Example 10 except for changing the reaction solvent to ethyl acetate, a colorless oily compound mentioned above (1.24 g, 89.5%) was obtained. The optical purity of the product obtained was 99.9% e.e. as determined by HPLC.

EXAMPLE 12

Preparation of (R,S)-3-chlorostyrene Oxide

According to the same method as in Example 9 except for changing the reaction solvent to t-butyl methyl ether and changing the starting material to (R,S)-2-(3-chlorophenyl)-2-(3,4,5,6-tetrahydro-[2H]-pyran-2-yloxy)ethyl methanesulfonate, a colorless oily compound mentioned above (1.25 g, 90.2%) was obtained.

EXAMPLE 13

Preparation of (R)-3-chlorostyrene Oxide

Into toluene (1,000 ml) were added (R)-3-chloromandelic acid (10 g) and p-toluenesulfonic acid (0.2 g), and the resulting mixture was stirred at 70° C. for 2 hours. The solvent was distilled off under reduced pressure. To the residue were added toluene (100 ml) and then, under ice-cooling and dropwise, 3,4-dihydro-2H-pyran (5.0 g), and the resulting mixture was stirred at the same temperature for 1 hour. The reaction mixture was washed with a saturated aqueous sodium hydrogen carbonate solution, then the organic layer was further washed with a saturated aqueous sodium chloride solution and dried with anhydrous magnesium sulfate. The desiccant was filtered off and then a 70% sodium dihydrobis(2-methoxyethoxy)aluminate toluene solution (16.7 g) was dropwise added to the filtrate with ice-cooling. The resulting mixture was stirred at the same temperature for 1 hour. The reaction mixture was added into a 30% aqueous (+)–potassium sodium tartrate solution (60.0 g), stirred for 1 hour and then the organic layer was separated. The organic layer obtained was washed with water and further with a saturated aqueous sodium chloride solution and then dried with anhydrous magnesium sulfate. The desiccant was filtered off. Then, to the filtrate were added triethylamine (10.8 g) and, under ice-cooling and dropwise, methanesulfonyl chloride (6.42 g). The resulting mixture was stirred at the same temperature for 1 hour, the reaction mixture was washed with water, then methanol (20 ml) and p-toluenesulfonic acid (10.4 g) were added thereto, and the resulting mixture was stirred at 50° C. for 1 hour. The reaction mixture was washed with water, then a 20% aqueous NaOH solution (40 g) was added thereto under ice-cooling, and the resulting mixture was stirred at the same temperature for 2 hours. The reaction mixture was washed with water, further the organic layer was washed with a saturated aqueous sodium chloride solution and dried with anhydrous magnesium sulfate. The desiccant was filtered off, then the solvent was distilled off under reduced pressure, and the resulting oily substance was distilled under reduced pressure to obtain a colorless oily compound mentioned above (6.6 g, yield 79.7%). The optical purity of the product obtained was 99.9% e.e. as determined by HPLC.

Comparative Example 1 Preparation of (R)-3-chlorostyrene oxide

1) Preparation of (R)-2-(3-chlorophenyl)-2-hydroxyethanol

Into THF (70 ml) were added (R)-3-chloromandelic acid (10 g) and further, under ice-cooling and dropwise, a 1M-diborane THF solution (81.5 ml) over 2 hours, and then stirring was continued at 25° C. for 12 hours. The reaction mixture was cooled, methanol (20 ml) was added thereto over 30 minutes and then stirring was further continued for 3 hours. The resulting reaction mixture was concentrated and then the residue was recrystallized from diethyl ether to obtain a colorless oily compound mentioned above (7.3 g, 78.9%).

2) Preparation of (R)-2-(3-chlorophenyl)-2-hydroxyethyl methanesulfonate

Into toluene (30 ml) were added (R)-2-(3-chlorophenyl)-2-hydroxyethanol obtained in 1) above (7 g), pyridine (8.0 g) and further, under ice-cooling and dropwise, p-toluenesulfonyl chloride (9.3 g), and then the resulting mixture was stirred at the same temperature for 24 hours. The solid thus precipitated was filtered off, the filtrate was concentrated, and the residue was dissolved in toluene (40 ml) and then washed with dilute hydrochloric acid. The organic layer was collected by layer separation, washed with a saturated aqueous sodium chloride solution and dried with anhydrous magnesium sulfate. The desiccant was filtered off, the solvent was distilled off under reduced pressure, and the residue was recrystallized from diethyl ether and hexane to obtain a colorless oily compound mentioned above (10.6 g, 80.0%).

3) Preparation of (R)-3-chlorostyrene oxide

Into dimethyl sulfoxide (30 ml) were added (R)-2-(3-chlorophenyl)-2-hydroxyethyl methanesulfonate obtained in 2) above (10 g) and, under ice-cooling, a 5N aqueous NaOH solution (15 ml), and then the resulting mixture was stirred at the same temperature for 12 hours. The reaction mixture was added into ice water and extracted with 50% diethyl ether/pentane. The organic layer was washed with a saturated aqueous sodium chloride solution and then dried with anhydrous magnesium sulfate. The desiccant was filtered off, then the solvent was distilled off under reduced pressure, and the oily substance obtained was distilled under reduced pressure to obtain a colorless oily compound mentioned above (3.62 g, 76.5%). The optical purity of the product obtained was 97.5% e.e. as determined by HPLC.

INDUSTRIAL APPLICABILITY

This invention relates to an acetalsulfonate derivative useful as a raw material for medicines, agricultural chemicals, etc., and can provide an acetalsulfonate derivative in high yield and high purity. According to this invention, from an acetal sulfonate derivative or a mandelic acid derivative as a starting material, an intended styrene oxide derivative can be obtained in high yield and in high purity and, when the acetalsulfonate derivative or the mandelic acid derivative of the starting material is an optically active substance, a corresponding styrene oxide derivative can be obtained while retaining the configuration.

Further, the process of this invention is suitable as a simple and economical industrial process of high safety.

What is claimed is:

1. A process for producing a styrene oxide derivative represented by the following formula (6)

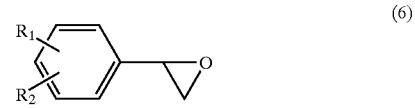

(6)

wherein $R_1$ and $R_2$ are the same as defined above, which comprises:

(e) a deprotecting step of deprotecting an acetalsulfonate derivative represented by the following formula (1)

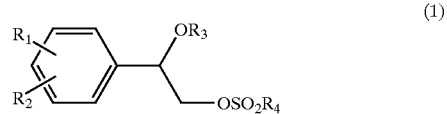

(1)

wherein $R_1$, $R_2$, $R_3$ and $R_4$ are the same as defined above, and (f) an epoxidizing step of epoxidizing a sulfonate derivative represented by the following formula (7) obtained in the above-mentioned deprotecting step with the aid of a base catalyst

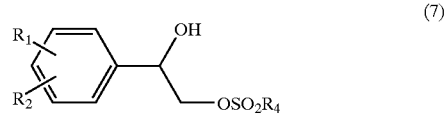

(7)

wherein $R_1$, $R_2$ and $R_4$ are the same as defined above.

2. The process for producing a styrene oxide derivative according to claim 1 wherein the compounds represented by the above formulas (1), (6) and (7) are each of an R-configuration.

3. The process for producing a styrene oxide derivative according to claim 1 wherein the compounds represented by the above formulas (1), (6) and (7) are each of an S-configuration.

4. The process for producing a styrene oxide derivative according to claim 1 wherein $R_3$ is 3,4,5,6-tetrahydro-2H-pyran-2-yl group.

5. The process for producing a styrene oxide derivative according to claim 1 wherein $R_3$ is 1-methoxy-1-methylethyl group.

6. The process for producing a styrene oxide derivative according to claim 1 wherein $R_4$ is methyl group.

7. The process for producing a styrene oxide derivative according to claim 1 wherein $R_4$ is p-tolyl group.

8. The process for producing a styrene oxide derivative according to claim 1 wherein both $R_1$ and $R_2$ are a hydrogen atom.

9. The process for producing a styrene oxide derivative according to claim 1 wherein one of $R_1$ and $R_2$ is a hydrogen atom and the other is a chlorine atom.

10. A process for producing a styrene oxide derivative represented by the following formula (6)

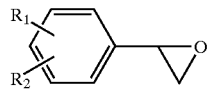
(6)

wherein $R_1$ and $R_2$ are the same as defined above, which comprises:
(a) a first step of esterifying a mandelic acid derivative represented by the following formula (2)

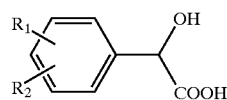
(2)

wherein $R_1$ and $R_2$ are the same as defined above,
(b) a second step of protecting by an acetal a mandelic ester derivative represented by the following formula (3) obtained in the first step

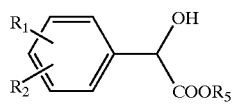
(3)

wherein $R_1$, $R_2$ and $R_5$ are the same as defined above, (c) a third step of reducing an acetal derivative represented by the following formula (4) obtained in the second step

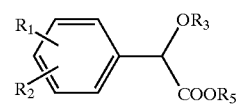
(4)

wherein $R_1$, $R_2$, $R_3$ and $R_5$ are the same as defined above,
(d) a fourth step of reacting with a sulfonyl chloride derivative an ethanediol derivative represented by the following formula (5) obtained in the third step

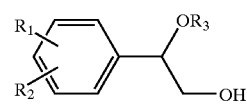
(5)

wherein $R_1$, $R_2$ and $R_3$ are the same as defined above,
(e) a deprotecting step of deprotecting an acetalsulfonate derivative represented by the following formula (1) obtained in the fourth step

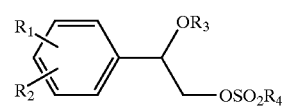
(1)

wherein $R_1$, $R_2$, $R_3$ and $R_4$ are the same as defined above, and
(f) an epoxidizing step of epoxidizing a sulfonate derivative represented by the following formula (7) obtained in the above-mentioned deprotecting step, with the aid of a base catalyst

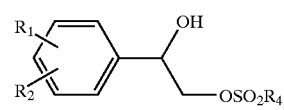
(7)

wherein $R_1$, $R_2$ and $R_4$ are the same as defined above.

* * * * *